United States Patent
Timmer et al.

(10) Patent No.: US 7,920,672 B2
(45) Date of Patent: Apr. 5, 2011

(54) X-RAY DETECTOR GAIN CALIBRATION DEPENDING ON THE FRACTION OF SCATTERED RADIATION

(75) Inventors: Jan Timmer, Eindhoven (NL); Peter George Van De Haar, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 87 days.

(21) Appl. No.: 12/374,391

(22) PCT Filed: Jul. 10, 2007

(86) PCT No.: PCT/IB2007/052723
§ 371 (c)(1),
(2), (4) Date: Jan. 20, 2009

(87) PCT Pub. No.: WO2008/012710
PCT Pub. Date: Jan. 31, 2008

(65) Prior Publication Data
US 2009/0310754 A1 Dec. 17, 2009

(30) Foreign Application Priority Data
Jul. 20, 2006 (EP) .................................. 06117528

(51) Int. Cl.
G01D 18/00 (2006.01)
H05G 1/64 (2006.01)
(52) U.S. Cl. .......................... 378/7; 378/207; 250/252.1
(58) Field of Classification Search .............. 378/7, 154, 378/207; 250/252.1
See application file for complete search history.

(56) References Cited

U.S. PATENT DOCUMENTS

| | | | | |
|---|---|---|---|---|
| 4,891,829 A | | 1/1990 | Deckman et al. | |
| 6,157,700 A | * | 12/2000 | Sako | 378/98.12 |
| 6,396,074 B1 | * | 5/2002 | Tsujii | 250/582 |
| 6,789,943 B2 | | 9/2004 | Zapalac | |
| 6,819,786 B2 | * | 11/2004 | Hirai | 382/132 |
| 6,868,137 B2 | * | 3/2005 | Inoue | 378/98.4 |
| 7,075,061 B2 | * | 7/2006 | Spahn | 250/252.1 |
| 7,119,327 B2 | * | 10/2006 | Spahn et al. | 250/252.1 |
| 7,142,705 B2 | * | 11/2006 | Inoue et al. | 382/132 |
| 7,221,735 B2 | * | 5/2007 | Inoue | 378/97 |
| 7,734,009 B2 | * | 6/2010 | Brunner et al. | 378/62 |
| 2003/0072409 A1 | | 4/2003 | Kaufhold et al. | |
| 2005/0078787 A1 | | 4/2005 | Dinten et al. | |
| 2005/0092909 A1 | | 5/2005 | Spahn | |
| 2005/0243963 A1 | | 11/2005 | Ghelmansarai et al. | |
| 2006/0002505 A1 | | 1/2006 | Saito | |

FOREIGN PATENT DOCUMENTS

EP  1553407 A1  7/2005
WO  2005006257 A2  1/2005

OTHER PUBLICATIONS

Zellerhoff M. et al.: "Low contrast 3D-reconstruction from C-arm data" Proceedings of SPIE, Medical Imaging 2005: Physics of Medical Imaging, vol. 5745, Apr. 2005, pp. 646-655, XP002459510.

* cited by examiner

Primary Examiner — Allen C. Ho

(57) ABSTRACT

It is described a gain calibration for a two-dimensional X-ray detector (315), in which the gain coefficients for scattered radiation (307b) and direct radiation (307a) are measured or estimated separately. A weighed average may be applied on the appropriate scatter fraction. The scatter fraction depending gain calibration method produces less ring artifacts in X-ray images as compared to known gain calibration methods, which do not take into account the fraction of scattered radiation reaching the X-ray detector (315).

20 Claims, 6 Drawing Sheets

X-RAY DETECTOR GAIN CALIBRATION DEPENDING ON THE FRACTION OF SCATTERED RADIATION

The present invention relates to the field of image processing of digital X-ray images, which have been recorded by means of an X-ray apparatus comprising an X-ray source and a two-dimensional X-ray detector having a spatial resolution. In particular the present invention relates to a gain calibration method for a two-dimensional resolving X-ray detector being used preferably for medical X-ray imaging.

Further, the present invention relates to a method for obtaining a gain corrected X-ray image of an object under examination.

The present invention further relates to a data processing device and to a medical X-ray imaging apparatus for determining a gain dataset representing gain coefficients of a two-dimensional X-ray detector being in particular used for medical X-ray imaging.

Furthermore, the present invention relates to a computer-readable medium and to a program element having instructions for executing the above-mentioned method for determining a gain dataset representing gain coefficients of a two-dimensional X-ray detector.

US2003/0072409 A1 discloses a method for estimating a material composition of an imaged object using an X-ray imaging system. Thereby, a plurality of scatter-corrected and gain-corrected reference calibration images are generated. The reference image correction includes removing the effects of electronic drift in digital detector over time, geometric effects, and non-uniform detector counting characteristics, which are spatially varying over the digital detector. The radiation incident on the detector is either "primary" or "scattered". This means that each X-ray photon can either pass through the material directly and not scatter or it can deflect off of some nuclei and scatter at least once. The scattered radiation is estimated and removed from the reference calibration images using a scatter-correction algorithm.

U.S. Pat. No. 6,789,943 B2 discloses a method and an X-ray apparatus for scatter measurements using an occluded detector ring. The method includes performing a calibration scan using a phantom to measure a scatter signal ratio between scattered X-rays impacting a first detector ring and scattered X-rays impacting a second detector ring. The scatter signal ratio is used to determine a scatter scale factor.

Gain calibration is a known and essential step in the raw data pre-processing for CT and/or X-ray data in order to reconstruct high quality three-dimensional (3D) representations of an object under examination. A gain calibration comprises the determination of different gain coefficients for different detector elements of a two-dimensional spatial resolving X-ray detector, wherein the different detector elements have a different sensitivity for detecting X-radiation. Of course, also electronic circuits for reading out these detector elements and/or for amplifying signals provided by these detector elements may contribute to a different effective X-ray sensitivity.

An appropriate gain calibration allows to provide a so called Hounsfield scale for the 3D data. The Hounsfield scale is a quantitative scale for describing the radiodensity respectively the relative transparency of a human or animal tissue. Thereby, a Hounsfield Unit (HU) of −1000 is assigned to air and a HU of 0 is assigned to water.

Further, an appropriate gain calibration may contribute to reduce many artifacts found in X-ray images such as e.g. shading, capping and cupping, streaks and rings. However, even if known gain calibration procedures improve the quality of X-ray images, significant ring artifacts are still left especially when an anti-scatter grid is used.

There may be a need for providing an X-ray detector gain calibration, which allows for a further reduction of in particular ring artifacts.

This need may be met by the subject matter according to the independent claims. Advantageous embodiments of the present invention are described by the dependent claims.

According to first aspect of the invention there is provided a method for determining a gain dataset representing gain coefficients of a two-dimensional X-ray detector, in particular a two-dimensional X-ray detector array being used for medical X-ray imaging. The described method comprises the steps of (a) providing a first gain dataset representing a first X-ray image, which is generated by direct X-radiation being emitted from an X-ray source and detected by the X-ray detector in the absence of an object of interest, (b) obtaining a second gain dataset representing a second X-ray image, which is based on scattered X-radiation being emitted from the X-ray source and detected by the X-ray detector in the presence of a predetermined object, and (c) combining the first gain dataset with the second gain dataset to give the final gain dataset.

This aspect of the invention is based on the idea that the X-ray image of the predetermined object is the sum of a direct image being acquired by X-radiation impinging directly onto the detector and a scattered image being acquired by X-radiation being scattered at least once by nuclei of an object under examination before impinging onto the detector. In this respect it has been found out by the inventors that the fraction of an X-ray image, which is based on scattered X-rays, comprises only a negligible structured noise. Therefore, for determining a gain datasets it is beneficial to individually take into account two different types of radiation being measured by the X-ray detector. First the direct radiation typically showing a significant structured noise and second the scattered radiation typically showing a negligible structured noise only.

In other words, it has been found out that with respect to a gain calibration a first contribution to an X-ray image showing little or no structured noise may be treated in a different way as compared to a second contribution showing a comparatively intense structured noise having typically a comparatively high spatial frequency. Thereby, the first contribution is predominately based on scattered radiation, whereas the second contribution to the X-ray image is based predominately on direct radiation. This individual treatment of different types of image contribution showing different structured noise provides for a further artifact reduction as compared to known gain calibration methods.

By contrast to e.g. thermal noise the structured noise is temporally constant. The structured noise may be caused e.g. by an X-radiation profile having a spatial frequency. Such a spatial frequency may be caused for instance by a hot cathode of an X-ray tube, wherein the hot cathode comprises a spatial non-uniform release of electrons e.g. due to different temperatures of the hot cathode and/or due to the given geometry of the hot cathode. Since structured noise typically has a high spatial frequency it is difficult to remove it from an X-ray image. This holds in particular if the spatial frequency of the structured noise is similar to the spatial frequency of image structures, which are supposed to be resolved within the X-ray image.

However, structured noise may also be caused by a spatially varying sensitivity of the X-ray detector leading to e.g. ring type artifacts in the final processed X-ray image. Since the first X-ray image is predominately based on direct radiation reaching the X-ray detector, the described method provides for an improved gain calibration wherein the gain coefficients for direct radiation and scattered radiation are taken into account separately. This has the advantage that many artifacts, which are to be found in X-ray images, and in particular ring artifacts can be reduced significantly.

In principle the gain dataset may comprise a gain coefficient assigned to each pixel element of the X-ray detector. However, in practice it has turned out that typically the gain coefficients are constant with certain areas of the detector. Such areas may be defined by detector pixel elements, which are assigned to an individual electronic circuit for reading out the corresponding signals of the detector pixel elements. Thereby, these signals represent the X-ray intensity being measured by each detector pixel.

It has to be pointed out that the acquired gain coefficients are used for image processing an acquired X-ray image representing the X-ray attenuation of the predetermined object. Typically, the gain coefficients are not used for any amplifiers or pre-amplifiers being connected to each detector pixel. However, the described method may also be used in order to perform a spatially varying calibration of gain coefficients of electronic amplification devices being connected with the detector pixel elements.

In this respect it is pointed out that the term "obtaining" is used in order to describe a variety of different measures for receiving the second gain dataset. For instance the term "obtaining" can mean measuring, i.e. the second gain dataset is experimentally recorded in particular by using the same object, which is supposed to be X-ray imaged. However, the term "obtaining" also includes an estimation procedure wherein, based on experts knowledge, the second gain dataset is simulated e.g. by using a standard phantom representing a model of the object, which is supposed to be X-ray imaged.

According to an embodiment of the invention the X-ray detector is used in connection with an anti scatter grid. In this context an anti scatter grid is any channel type X-ray absorption device providing for an X-ray attenuation, which compared to direct X-rays is different for scattered X-rays impinging onto the detector under at least a slightly slanted angle.

It has been realized by the inventors that the combination of the X-ray detector with an anti-scatter grid has a different sensitivity for scattered X-rays than for direct radiation impinging onto the detector without being scattered in particular by the object of interest. This different sensitivity can be understood because the anti scatter grid introduces a structured noise having a comparatively high spatial frequency. Although at a first glance the differences in the sensitivity are not big, it has turned out that these differences are large enough in order to produce ring type artifacts. The different sensitivity of the X-ray detector being equipped with an anti-scatter grid is compensated at least partially by spatially varying gain coefficients being used for further image processing. Therefore, artifacts and in particular ring artifacts may be reduced significantly.

It has to be pointed out that even in the presence of an anti scatter grid there is still a contribution of scattered radiation when an X-ray image is acquired. Depending on the size, on the material and on the scattering properties of the object under study the fraction of scattered radiation compared to the total X-radiation impinging onto the X-ray detector is in the order of 10% to 100%. Of course, an anti scatter grid allows for a further suppression of scattered radiation. However, such anti scatter grids reduce also the direct radiation such that in order to acquire X-ray images with a comparatively low statistic noise one has to increase the overall radiation dose for an object under examination. However, in case of medical X-ray imaging such an increase of the radiation dose is typically not acceptable for human beings.

According to a further embodiment of the invention the step of obtaining a second gain dataset comprises acquiring the second gain dataset by an experimental recording of the predetermined object, wherein direct X-radiation is prevented from being impinged onto the detector. This may provide the advantage that the contribution of scattered radiation to the X-ray image of the object may be determined very precisely. Therefore, in the case of medical X-ray imaging a patient individual gain calibration may be realized such that in particular ring artifacts may be removed or reduced in a very effective manner. A proper measurement of the sensitivity of the X-ray detector both for direct and for scattered X-rays may lead to an in particular strong reduction of ring artifacts.

In this respect it is clear that during the experimental data acquisition the object under study is placed within the radiation paths in between the X-ray source and the X-ray detector.

There are various known ways how to selectively obtain an X-ray image based predominately on scattered radiation. One in particular effective way is to use an X-ray blocking device, which is placed in between the X-ray source and the X-ray detector. Thereby, X-rays being measured in the shadow of the X-ray blocking device have to be scattered X-rays. A further effective method may be carried out by using a collimated X-ray beam. Thereby, for acquiring the second gain dataset only the signals of detector elements are taken into account, which are located outside the direct collimated X-ray beam. Of course, in order to acquire a full two-dimensional scattered X-ray image the collimated X-ray beam may be sequentially directed to various different spatial regions on the X-ray detector.

According to a further embodiment of the invention the step of combining the first gain dataset with the second gain dataset comprises adding the first gain dataset and the second gain dataset. This has the advantage that the gain data set combination is a simple mathematical operation, which may be implemented easily in current known and widely available image processing routines. Therefore, the described method may be realized by means of a rather simple software modification of standard X-ray image processing methods.

Since typically the direct X-radiation is more intense than the scattered X-radiation, which is in particular true when an anti scatter grid is used and a small object like a human head is scanned, the second gain dataset may be interpreted as containing Offset values for the gain coefficients of the first gain dataset.

According to a further embodiment of the invention the step of obtaining a second gain dataset comprises estimating the second gain dataset by using the fraction of scattered X-radiation being detected by the X-ray detector as compared to the total X-radiation being detected by the X-ray detector. This may provide the advantage that no extra radiation dose for e.g. a patient under examination is required in order to obtain the second gain dataset. Thereby, the estimation procedure may be based on expert and/or empiric knowledge, which is also available by means of standard phantoms corresponding to the real object of interest. Nowadays, appropriate phantoms are available for all parts of in particular a human body. These phantoms include a composition of different materials, which exhibit at least within the diagnostically relevant energy range a similar X-ray attenuation or X-ray absorption behavior compared to the object of interest. Common materials are for instance water and calcium.

Of course, the fraction of scattered radiation not only depends on the type of material representing the phantom, the fraction of scattered radiation also depends on the photon energy and/or the photon energy distribution of the X-radiation impinging onto the real object. However, these dependencies are well known such that for each experimental condition an appropriate scatter fraction may be estimated. A typical value for the fraction of scattered X-radiation is e.g. 30%. This means that 70% of the X-radiation being detected by the X-ray detector is direct X-radiation.

Preferably, the fraction of scattered radiation compared to the total radiation being detected by the X-ray detector is estimated within an area of interest representing a relevant portion of the object under examination.

According to a further embodiment of the invention the fraction of scattered X-radiation is determined by means of averaging the intensity of the scattered radiation within a predefined area of interest. This may provide the advantage that the fraction of scattered radiation can be estimated selectively within a diagnostically relevant area. Therefore, the reduction of artifacts may be focused on a certain part of a human body such that in particular the diagnostically relevant area within an X-ray image is deteriorated as little as possible in order to improve the diagnostic recognizability as far as possible.

According to a further embodiment of the invention the second gain dataset comprises uniform pixel values representing a homogeneous second X-ray image. This means that the first gain dataset is combined with a non-structured second image.

In case the combination of the two gain datasets is a simple addition of the two datasets the second gain dataset simply represents a spatially constant offset. Although such a spatially uniform offset seems to have only a little influence on the gain calibration, it has turned out that, when the described gain calibration is carried out, an artifact reduction by a factor of approximately 2 may be achieved.

According to a further embodiment of the invention the uniform pixel values are obtained by means of an averaging procedure, which is carried out within the first X-ray image and/or within the second X-ray image. This may provide the advantage that the non-structured second X-ray image can be obtained with a rather simple mathematical operation, whereby an appropriate uniform gain correction factor is obtained leading to reduced X-ray image artifacts. Thereby, the averaging procedure can be carried out within at least a predetermined area of interest within the first and/or the second X-ray image.

According to a further embodiment of the invention the step of combining the first gain dataset with the second gain dataset comprises adding the first gain dataset and the second gain dataset. This has the advantage that the gain data set combination is a simple mathematical operation, which may be implemented easily in current known and widely available image processing routines. Therefore, the described method may be realized by means of a rather simple software modification of standard X-ray image processing methods.

According to a further embodiment of the invention the step of adding the first gain dataset and the second gain dataset comprises (a) taking into account the first gain dataset with a first weighing factor representing the fraction of direct radiation as compared to the total radiation impinging onto the X-ray detector and (b) taking into account the second gain dataset with a second weighing factor representing the fraction of scattered radiation as compared to the total radiation impinging onto the X-ray detector. Such an appropriate weighing of the two datasets may provide the advantage that a significantly improved gain calibration can be obtained resulting in a further reduction of in particular ring artifacts.

According to a further aspect of the present invention there is described a method for obtaining a gain corrected X-ray image of an object under examination. The described method comprises the steps of (a) determining a gain dataset representing the gain coefficients of a two-dimensional X-ray detector by carrying out exemplary embodiments of the above-described method, (b) acquiring a third dataset representing an X-ray image of the object under examination, which has been inserted in between the X-ray source and the X-ray detector, and (c) obtaining a gain corrected dataset representing a gain corrected image of the object under examination by dividing the third dataset through the gain dataset.

This aspect of the invention is based on the idea that by carrying out the above-described method or by carrying out embodiments of the above-described method for determining a gain dataset improved X-ray images showing significantly reduced artifacts may be obtained.

According to an embodiment of the invention the obtained X-ray image is used for a three-dimensional reconstruction of the object under examination. Thereby, of course a plurality of different gain corrected datasets, which have been acquired under different projection angles, may be used for the three-dimensional image reconstruction. Preferably, all of these gain corrected datasets have been obtained by carrying out the above-described method for obtaining a gain corrected X-ray image of an object under examination.

In this respect it is pointed out that image artifacts such as undesired ring structures are typically much more noticeable in three-dimensional reconstructed images than in two-dimensional X-ray images. In this respect it has turned out that even if within the two-dimensional X-ray images structured noise cannot be seen they nonetheless may be noticeable in a three-dimensional representation of the corresponding object, wherein the image reconstruction is based on a plurality of these two-dimensional images. Therefore, the above-described method may be widely used for significantly improving the quality of three-dimensional reconstructed images. In particular, the above-described method provides a significant reduction of artifacts for so-called three-dimensional low contrast X-ray imaging, wherein due to low contrast images an artifact reduction causes a particular significant improvement of the resulting image quality.

It is pointed out that a three-dimensional image reconstruction may be based on a series of different projected two-dimensional images which have been obtained e.g. by means of a known computed tomography apparatus. However, since the mechanical precision of modern C-arm systems has also been improved recently, two-dimensional X-ray images being used for a three-dimensional image reconstruction may also be obtained by using a modern C-arm system.

According to a further aspect of the invention there is provided a data processing device for determining a gain dataset representing gain coefficients of a two-dimensional X-ray detector, in particular a two-dimensional X-ray detector array being used for medical X-ray imaging. The data processing device comprising (a) a data processor, which is adapted for performing exemplary embodiments of the above-described method, and (b) a memory for storing the first gain dataset representing the first X-ray image and the second gain dataset representing the second X-ray image.

According to a further aspect of the invention there is provided a medical X-ray imaging apparatus. The medical X-ray imaging apparatus is in particular a computed tomography scanner or a C-arm system. The medical X-ray imaging apparatus comprises the above described a data processing device.

According to a further aspect of the invention there is provided a computer-readable medium on which there is stored a computer program for determining a gain dataset representing gain coefficients of a two-dimensional X-ray detector, in particular a two-dimensional X-ray detector array being used for medical X-ray imaging. The computer program, when being executed by a data processor, is adapted for performing exemplary embodiments of the above-described methods.

According to a further aspect of the invention there is provided a program element for determining a gain dataset representing gain coefficients of a two-dimensional X-ray detector, in particular a two-dimensional X-ray detector array being used for medical X-ray imaging. The program element, when being executed by a data processor, is adapted for performing exemplary embodiments of the above-described methods.

The computer program element may be implemented as computer readable instruction code in any suitable programming language, such as, for example, JAVA, C++, and may be stored on a computer-readable medium (removable disk, volatile or non-volatile memory, embedded memory/processor, etc.). The instruction code is operable to program a computer or other programmable device to carry out the intended functions. The computer program may be available from a network, such as the WorldWideWeb, from which it may be downloaded.

It has to be noted that embodiments of the invention have been described with reference to different subject matters. In particular, some embodiments have been described with reference to method type claims whereas other embodiments have been described with reference to apparatus type claims. However, a person skilled in the art will gather from the above and the following description that, unless other notified, in addition to any combination of features belonging to one type of subject matter also any combination between features relating to different subject matters, in particular between features of the method type claims and features of the apparatus type claims is considered to be disclosed with this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

FIG. 2b shows a perspective view of the X-ray swing arm shown in FIG. 2a.

The illustration in the drawing is schematically. It is noted that in different figures, similar or identical elements are provided with the same reference signs or with reference signs, which differ from the corresponding reference signs only within the first digit.

Figure 1:
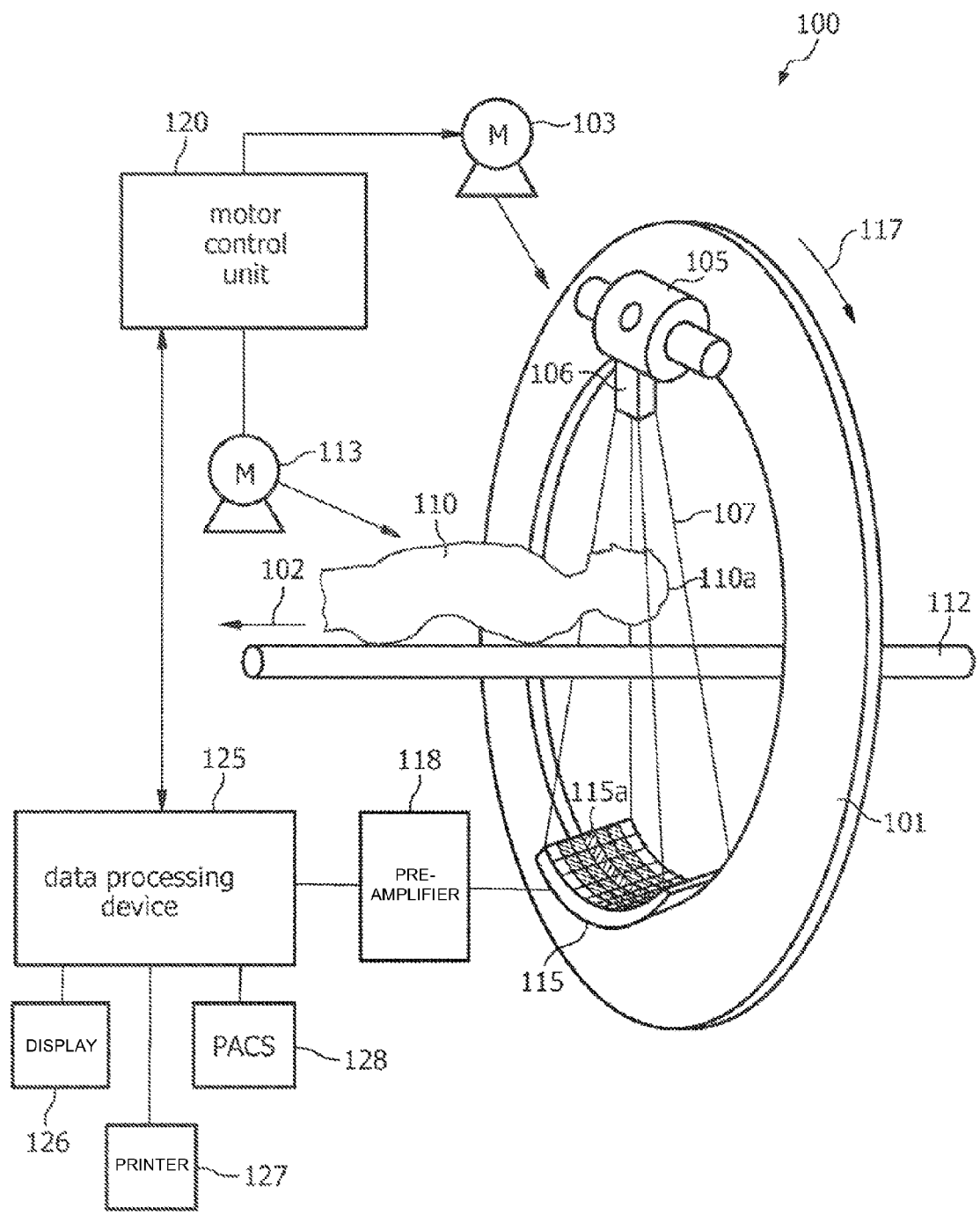
FIG. 1 shows a simplified schematic representation of a computed tomography (CT) system, which is adapted to perform a scatter fraction depending gain calibration.

FIG. 1 shows a computer tomography apparatus 100, which is also called a CT scanner. The CT scanner 100 comprises a gantry 101, which is rotatable around a rotational axis 102. The gantry 101 is driven by means of a motor 103.

Reference numeral 105 designates a source of radiation such as an X-ray source, which emits polychromatic radiation 107. The CT scanner 100 further comprises an aperture system 106, which forms the X-radiation being emitted from the X-ray source 105 into a radiation beam 107. The spectral distribution of the radiation beam emitted from the radiation source 105 may further be changed by a filter element (not shown), which is arranged close to the aperture system 106.

The radiation beam 107, which may be by a cone-shaped or a fan-shaped beam 107, is directed such that it penetrates a region of interest 110a. According to the embodiment described herewith, the region of interest is a head 110a of a patient 110.

The patient 110 is positioned on a table 112. The patient's head 110a is arranged in a central region of the gantry 101, which central region represents the examination region of the CT scanner 100. After penetrating the region of interest 110a the radiation beam 107 impinges onto a radiation detector 115. In order to be able to suppress X-radiation being scattered by the patient's head 110a and impinging onto the X-ray detector under an oblique angle there is provided a not depicted anti scatter grid. The anti scatter grid is preferably positioned directly in front of the detector 115.

The X-ray detector 115 is arranged on the gantry 101 opposite to the X-ray tube 105. The detector 115 comprises a plurality of detector elements 115a wherein each detector element 115a is capable of detecting X-ray photons, which have been passed through the head 110a of the patient 110.

During scanning the region of interest 110a, the X-ray source 105, the aperture system 106 and the detector 115 are rotated together with the gantry 101 in a rotation direction indicated by an arrow 117. For rotation of the gantry 101, the motor 103 is connected to a motor control unit 120, which itself is connected to a data processing device 125. The data processing device 125 includes a reconstruction unit, which may be realized by means of hardware and/or by means of software. The reconstruction unit is adapted to reconstruct a 3D image based on a plurality of 2D images obtained under various observation angles.

Furthermore, the data processing device 125 serves also as a control unit, which communicates with the motor control unit 120 in order to coordinate the movement of the gantry 101 with the movement of the table 112. A linear displacement of the table 112 is carried out by a motor 113, which is also connected to the motor control unit 120.

During operation of the CT scanner 100 the gantry 101 rotates and in the same time the table 112 is shifted linearly parallel to the rotational axis 102 such that a helical scan of the region of interest 110a is performed. It should be noted that it is also possible to perform a circular scan, where there is no displacement in a direction parallel to the rotational axis 102, but only the rotation of the gantry 101 around the rotational axis 102. Thereby, slices of the head 110a may be measured with high accuracy. A larger three-dimensional representation of the patient's head may be obtained by sequentially moving the table 112 in discrete steps parallel to the rotational axis 102 after at least one half gantry rotation has been performed for each discrete table position.

The detector 115 is coupled to a pre-amplifier 118, which itself is coupled to the data processing device 125. The processing device 125 is capable, based on a plurality of different X-ray projection datasets, which have been acquired at different projection angles, to reconstruct a 3D representation of the patient's head 110a.

In order to observe the reconstructed 3D representation of the patient's head 110a a display 126 is provided, which is coupled to the data processing device 125. Additionally, arbitrary slices of a perspective view of the 3D representation may also be printed out by a printer 127, which is also coupled to the data processing device 125. Further, the data processing device 125 may also be coupled to a picture archiving and communications system 128 (PACS).

It should be noted that monitor 126, the printer 127 and/or other devices supplied within the CT scanner 100 might be arranged local to the computer tomography apparatus 100. Alternatively, these components may be remote from the CT scanner 100, such as elsewhere within an institution or hospital, or in an entirely different location linked to the CT scanner 100 via one or more configurable networks, such as the Internet, virtual private networks and so forth.

Figure 2A:
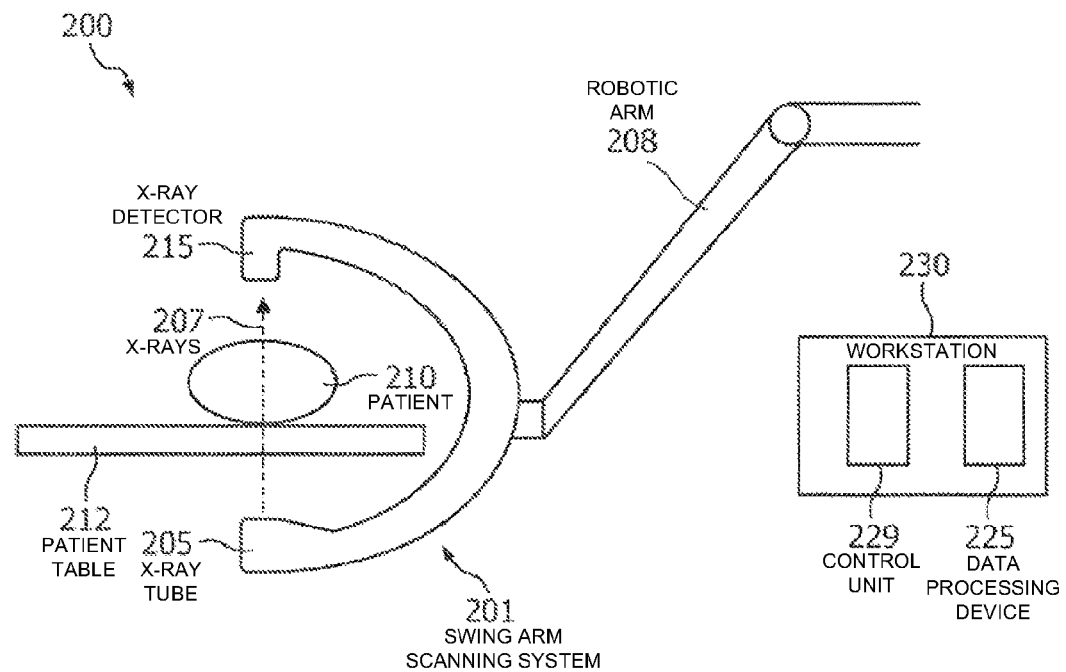
FIG. 2a shows a side view of a medical C-arm system, which is adapted to perform a scatter fraction depending gain calibration.
Figure 2B:
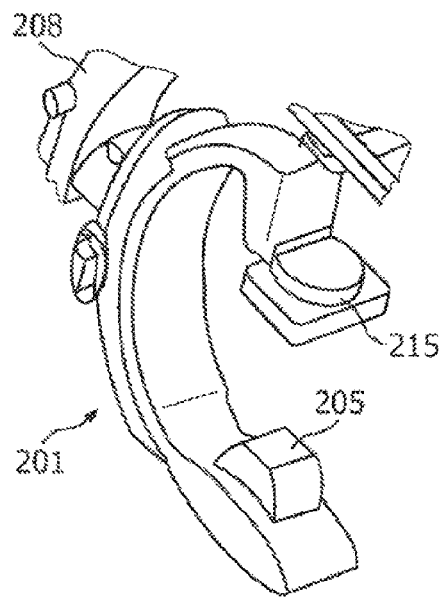

Referring to FIGS. 2a and 2b of the drawing, a medical X-ray imaging system 200 according to a further embodiment of the invention is a so called C-arm system. The C-arm system 200 comprises a swing arm scanning system 201 supported proximal a patient table 212 by a robotic arm 208. Housed within the swing C-arm 201, there is provided an X-ray tube 205 and an X-ray detector 215. The X-ray detector 215 is arranged and configured to detect X-rays 207, which have passed through a patient 210. Further, the X-ray detector 215 is adapted to generate an electrical signal representative of the intensity distribution thereof. By moving the swing arm 201, the X-ray tube 205 and the X-ray detector 215 can be placed at any desired location and orientation relative to the patient 210.

In order to be able to suppress X-radiation being scattered by the patient 210 and impinging onto the X-ray detector 215 under an oblique angle there may be provided a not depicted anti scatter grid. The anti scatter grid may be positioned directly in front of the detector 215.

The C-arm system 200 further comprises a control unit 229 and a data processing device 225, which are both accommodated within a workstation or a personal computer 230. The control unit 229 is adapted to control the operation of the C-arm system 200. The data processing device 225 is adapted for performing the scatter fraction dependent gain calibration method according to a preferred embodiment of the invention.

It is pointed out that the mechanical precision of the C-arm system 200 may be good enough in order to allow for a three-dimensional image reconstruction of the patient 210 based on a plurality of different projected two-dimensional images, which have been obtained by using the high precision C-arm system 200.

Figure 3:
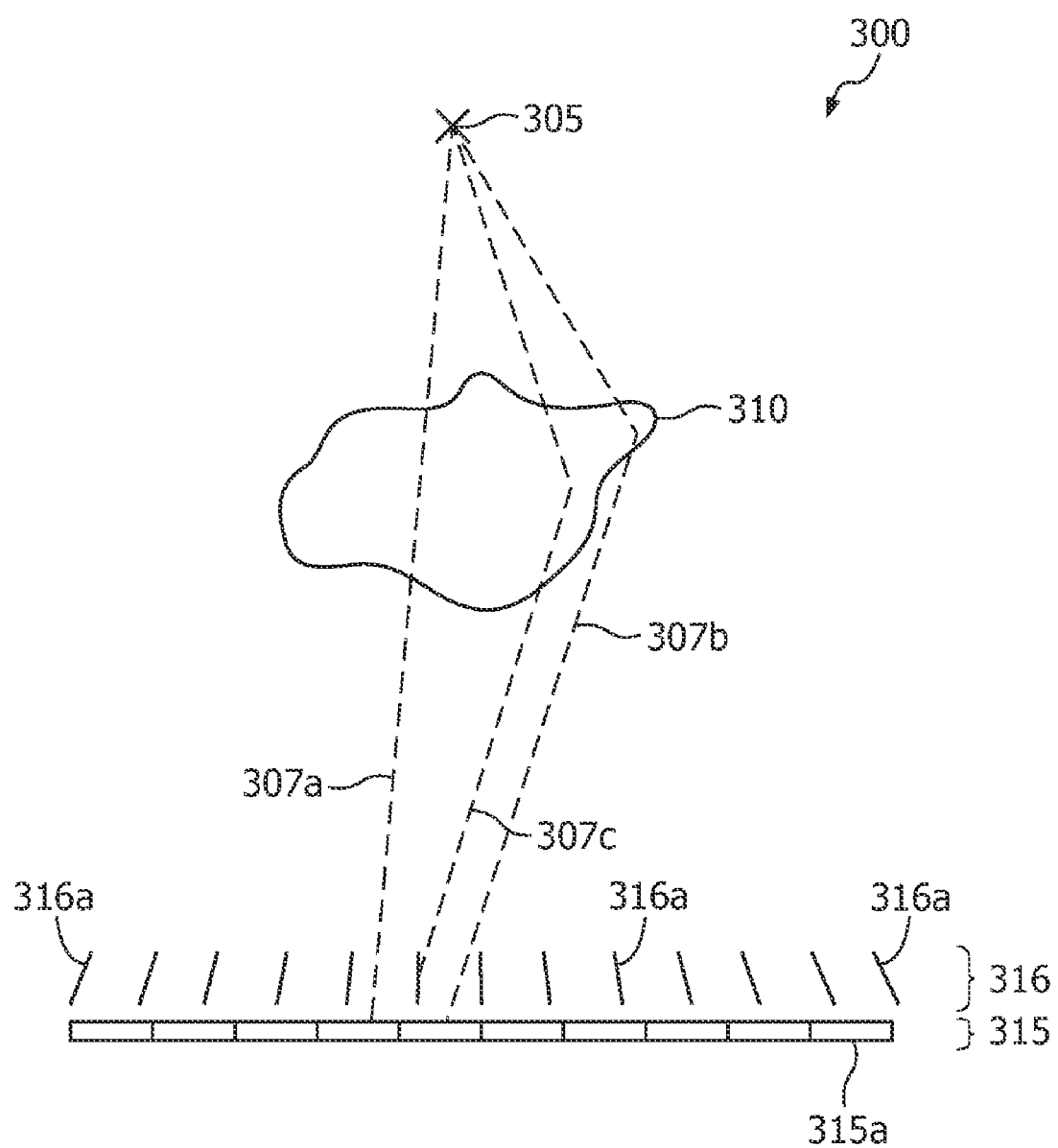
FIG. 3 shows a simplified representation of a medical X-ray imaging system comprising an X-ray source and a two-dimensional X-ray detector, which is equipped with an anti scatter grid.

FIG. 3 shows a simplified representation of a medical X-ray imaging system 300 comprising an X-ray source 305 and a two-dimensional X-ray detector 315, which is equipped with an anti scatter grid 316. The anti scatter grid 316 comprises a plurality of different lamellae 316a, which are oriented in an aligned manner with respect to the X-ray source 305. The lamellae 316a are preferably made of lead, which is accommodated within a non depicted matrix made of a X-ray transparent material such as plastic. The lamellae 316a have a height of approximately 3 mm and a thickness of approximately 0.1 mm. However, it is clear that also other geometries for the anti scatter grid may be applied.

Typically, the raster structure of the lamellae 316a is not adapted to the spacing between neighboring X-ray detection elements 315a. This holds in particular if the medical X-ray imaging system 300 is a C-arm system, because a C-arm system usually comprises a detector with a typical pixel size of approximately 0.18 mm. By contrast thereto, the lamellae 316a have a package density of typically 8 per mm. However, the raster structure of the lamellae 316a may also be adapted to the raster structure of the X-ray detection elements 315a. This holds in particular if the medical X-ray imaging system 300 is a CT scanner.

The anti scatter grid 316 is used for blocking X-rays 307c, which have been originated by the X-ray tube 305 and before reaching the detector 315 respectively the grid 316 have been scattered by nuclei of the patient 310, whereby the propagation direction of the X-ray 307c is changed significantly. Further, the anti scatter grid 316 is supposed to let direct X-rays 307a pass into the detector 315. However, the anti scatter grid 316 is never perfect such that it could happen that even if a scattered X-ray 307b has changed its propagation direction significantly it may occur that this X-ray 307b reaches the detector 315.

Figure 4:
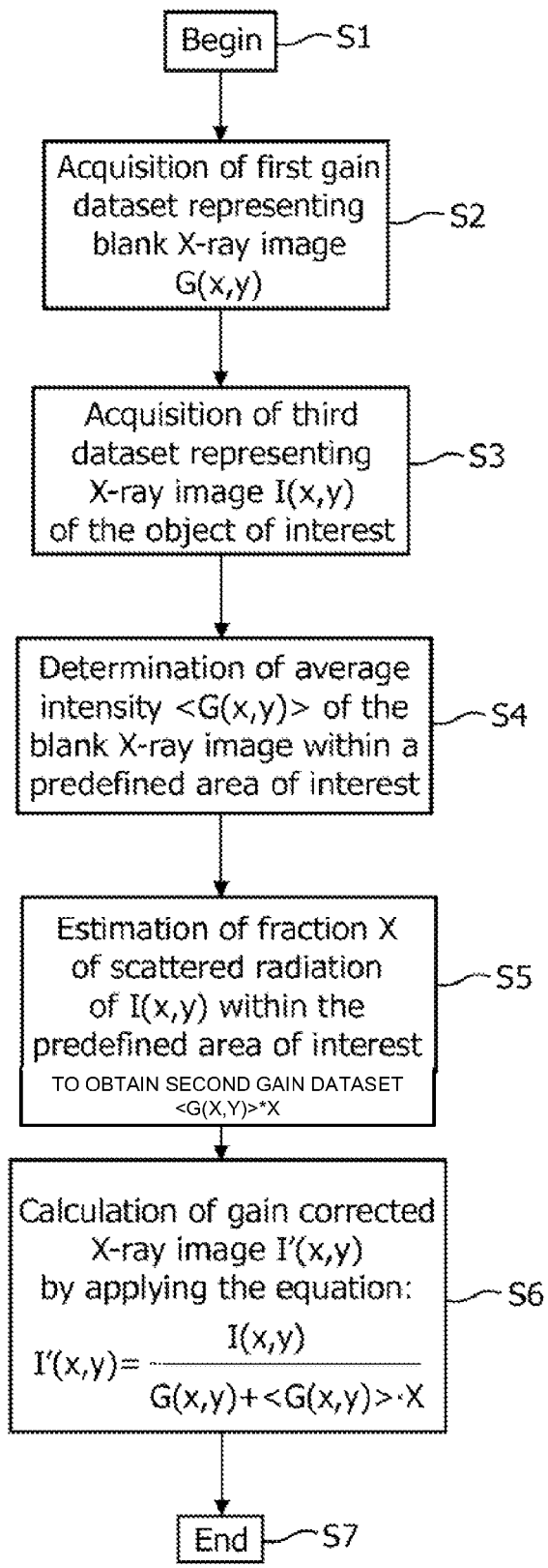
FIG. 4 shows a flow chart indicating method steps for performing a scatter fraction depending gain calibration according to a preferred embodiment of the invention.

FIG. 4 shows a flow chart on a method for performing a scatter fraction depending gain calibration according to a preferred embodiment of the invention. The method starts with a step S1.

In a next step S2 there is carried out a data acquisition of a first gain dataset representing a blank X-ray image $G(x,y)$. Thereby, the X-ray source emits X-radiation, which, because of the absence of any examination object in between the X-ray source and the X-ray detector, impinges onto the detector predominately as direct radiation. The fraction of scattered radiation being detected by the X-ray detector can be neglected, because air is only a very weak scattering medium for X-ray in the relevant diagnostic energy range. In order to allow for a precise gain correction an anti scatter grid is used already during the acquisition of the first gain dataset. The method continues with a step S3.

In step S3 there is carried out a data acquisition of a third dataset representing an X-ray image $I(x,y)$ of the object under examination. Thereby, the anti scatter grid is used in order to reduce the fraction of scattered radiation contributing to the X-ray image. The method continues with a step S4.

In step S4 there is determined the average intensity $<G(x,y)>$ of the blank X-ray image $G(x,y)$ within a predefined area of interest. Thereby, the area of interest corresponds to a diagnostically relevant area within the X-ray image $I(x,y)$. The method continues with a step S5.

In step S5 there is estimated a fraction X of scattered radiation of $I(x,y)$ within the predefined area of interest. Thereby, the estimation is based on expert knowledge. The estimation may be supported by a calculation of the scattering behavior of the X-radiation being incident on the object under examination. The calculation may be carried out by using appropriate standard phantoms showing similar X-ray scattering properties as compared to the real object under examination. The method continues with a step S6.

In step S6 there is performed a calculation of a gain corrected X-ray image $I'(x,y)$. Thereby, the following equation (1) is used:

$$I'(x, y) = \frac{I(x, y)}{G(x, y) + <G(x, y)> \cdot X} \quad (1)$$

The term "<G(x,y)>·X" can be understood as a second gain dataset, which represents a homogenous gain image having only one specific gain value. Since the contribution of scattered radiation is typically less than the contribution of direct radiation, the term "<G(x,y)>·X" represents an Offset value taking into account the fraction of scattered radiation contributing to the acquired X-ray image I(x,y).

Finally, the method ends with a step S7.

The described method has the advantage that is reduces the X-ray image artifacts and in particular ring artifacts significantly. Further, the described method can be carried out be applying rather simple mathematical operations. Therefore, the described scatter fraction dependent gain correction method may be implemented easily in current known and widely available image processing routines.

Figure 5:
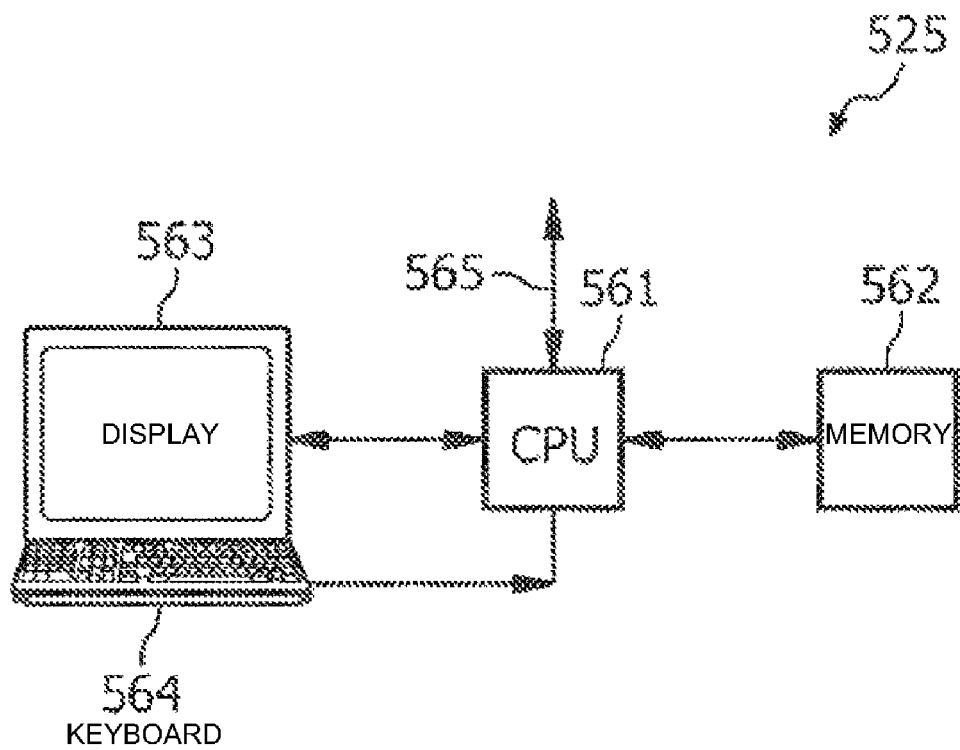
FIG. 5 shows a data processing device, which is adapted to perform a scatter fraction depending gain calibration.

FIG. 5 shows a data processing device 525, which is adapted to perform the above-described scatter fraction dependent gain calibration. The data processing device 525 comprises a central processing unit (CPU) or image processor 561. The image processor 561 is connected to a memory 562 for temporally storing acquired projection data. Via a bus system 565 the image processor 561 is connected to a plurality of input/output network or diagnosis devices, such as a CT scanner or a C-arm system. Furthermore, the image processor 561 is connected to a display device 563, for example a computer monitor, for displaying information or one or more images reconstructed by the image processor 561. An operator or user may interact with the image processor 561 via a keyboard 564 and/or any other output devices, which are not depicted in FIG. 5.

Figure 6A:
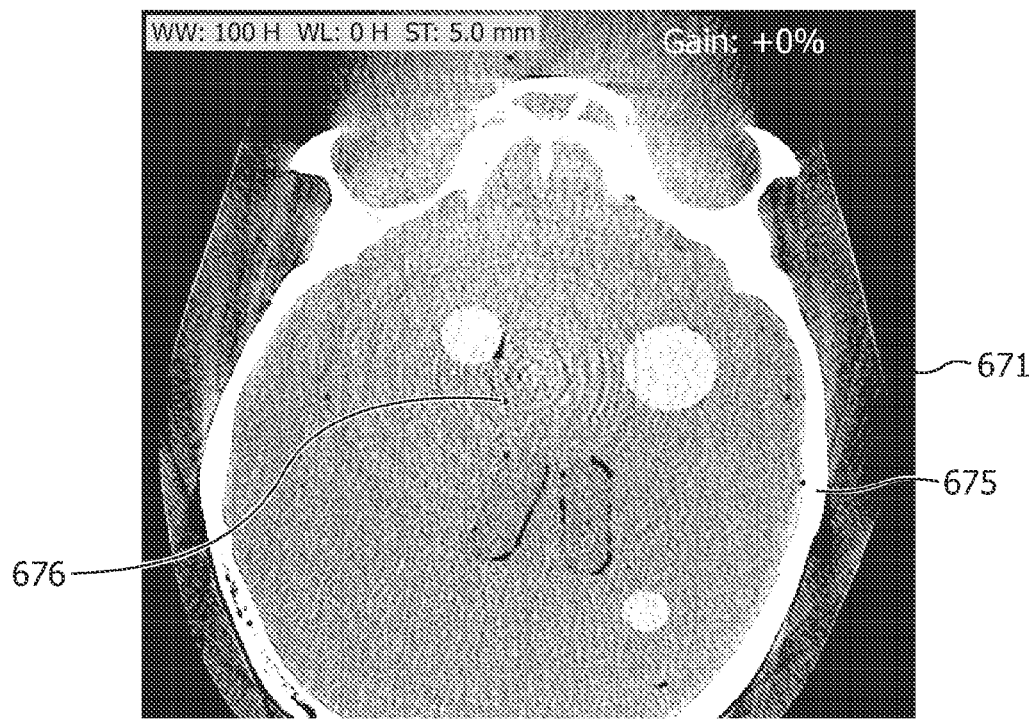
FIG. 6a shows a two-dimensional X-ray image, which has been obtained by employing a known gain calibration.

FIG. 6a shows a two-dimensional X-ray image 671 of a patient's head 675, which X-ray image 671 has been obtained by employing a known gain calibration method. In the center of the depicted patient's head 675 an artifact ring type structure 676 can be clearly seen.

Figure 6B:
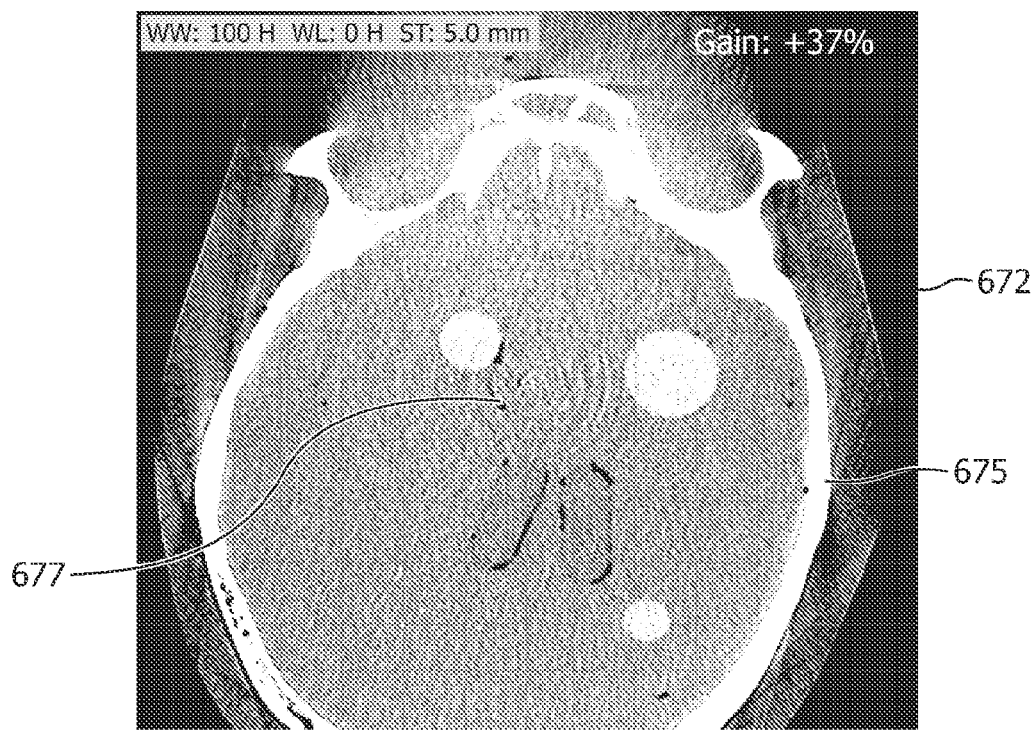
FIG. 6b shows a two-dimensional X-ray image, which has been obtained by employing a scatter dependent gain calibration according to a preferred embodiment of the invention.

FIG. 6b shows a two-dimensional X-ray image 672, which has been obtained by employing a significantly improved gain calibration method as described above as a preferred embodiment of the invention. Thereby, a different gain sensitivity for scattered X-radiation as compared to direct X-radiation has been taken into account. Within the patient's head 675, an artifact ring type structure 677 can still be seen. However, the ring structure is significantly less pronounced as compared to the ring structure 676 depicted in FIG. 6a.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

In order to recapitulate the above described embodiments of the present invention one can state:

It is described a gain calibration for a two-dimensional X-ray detector 315, in which the gain coefficients for scattered radiation 307b and direct radiation 307a are measured or estimated separately. A weighed average may be applied on the appropriate scatter fraction. The scatter fraction depending gain calibration method produces less ring artifacts in X-ray images as compared to known gain calibration methods, which do not take into account the fraction of scattered radiation reaching the X-ray detector 315.

LIST OF REFERENCE SIGNS 100 medical X-ray imaging system/computed tomography apparatus
101 gantry
102 rotational axis
103 motor
105 X-ray source/X-ray tube
106 aperture system
107 radiation beam
110 object of interest/patient
110a region of interest/head of patient
112 table
113 motor
115 X-ray detector
115a detector elements
117 rotation direction
118 Pulse discriminator unit
120 motor control unit
125 data processing device (incl. reconstruction unit)
126 monitor
127 printer
128 Picture archiving and communication system (PACS)
200 medical X-ray imaging system/C-arm system
201 swing arm scanning system/C-arm
205 X-ray source/X-ray tube
207 X-ray
208 robotic arm
210 object of interest/patient
212 table
215 X-ray detector
225 data processing device
229 control unit
230 workstation/personal computer
300 medical X-ray imaging system
305 X-ray source/X-ray tube
307a direct beam
307b scattered beam reaching the detector 315
307c scattered beam blocked by anti scatter grid 316
310 object of interest/patient
315 X-ray detector
315a detector elements
316 anti scatter grid
S1 begin
S2 step 2
S3 step 3
S4 step 4
S5 step 5
S6 step 6
S7 end
525 data processing device
561 central processing unit/image processor
562 memory
563 display device
564 keyboard
565 bus system
671 two dimensional X-ray image of a patients head without improved gain calibration
672 two dimensional X-ray image of a patients head with improved gain calibration
675 patients head
676 artifact ring type structure
677 reduced artifact ring type structure

The invention claimed is:

1. A method for determining a gain dataset representing gain coefficients of a two-dimensional X-ray detector being used for X-ray imaging, the method comprising:
   providing a first gain dataset representing a first X-ray image (G(x,y)), which is generated by direct X-radiation being emitted from an X-ray source and detected by the X-ray detector in the absence of an object of interest;
   obtaining a second gain dataset representing a second X-ray image, which is based on scattered X-radiation being emitted from the X-ray source and detected by the X-ray detector in the presence of a predetermined object; and
   combining the first gain dataset with the second gain dataset to obtain the gain dataset representing gain coefficients of the two-dimensional X-ray detector, wherein the gain dataset is configured for use in obtaining a gain corrected image of an object under examination by dividing a third dataset representing an X-ray image acquired for the object under examination by the gain dataset.

2. The method according to claim 1, wherein
   detecting the direct X-radiation and the scattered X-radiation via the X-ray detector includes using an anti scatter grid to provide an attenuation of scattered X-rays impinging onto the X-ray detector.

3. The method according to claim 1, wherein
   obtaining a second gain dataset comprises acquiring the second gain dataset by an experimental recording of the predetermined object, wherein direct X-radiation is prevented from being impinged onto the X-ray detector via the presence of the predetermined object within radiation paths between the x-ray source and the x-ray detector.

4. The method according to claim 3, wherein
   combining the first gain dataset with the second gain dataset comprises adding the first gain dataset and the second gain dataset.

5. A method for determining a gain dataset representing gain coefficients of a two-dimensional X-ray detector being used for X-ray imaging, the method comprising:
   providing a first gain dataset representing a first X-ray image (G(x,y)), which is generated by direct X-radiation being emitted from an X-ray source and detected by the X-ray detector in the absence of an object of interest;
   obtaining a second gain dataset representing a second X-ray image, which is based on scattered X-radiation being emitted from the X-ray source and detected by the X-ray detector in the presence of a predetermined object; and
   combining the first gain dataset with the second gain dataset to obtain the gain dataset, wherein
   obtaining the second gain dataset comprises estimating the second gain dataset by using the fraction of scattered X-radiation being detected by the X-ray detector as compared to the total X-radiation being detected by the X-ray detector.

6. The method according to claim 5, wherein
   the fraction of scattered X-radiation is determined by means of averaging the intensity of the scattered radiation within a predefined area of interest.

7. The method according to claim 5, wherein
   the second gain dataset comprises uniform pixel values representing a homogeneous second X-ray image.

8. The method according to claim 7, wherein
   the uniform pixel values are obtained by means of an averaging procedure, wherein the averaging procedure is carried out within one selected from the group consisting of (i) the first X-ray image, (ii) the second X-ray image and (iii) the first X-ray image and the second X-ray image.

9. The method according to claim 5, wherein
   combining the first gain dataset with the second gain dataset comprises adding the first gain dataset and the second gain dataset.

10. The method according to claim 9, wherein
    adding the first gain dataset and the second gain dataset comprises
    taking into account the first gain dataset with a first weighing factor representing the fraction of direct radiation as compared to the total radiation impinging onto the X-ray detector and
    taking into account the second gain dataset with a second weighing factor representing the fraction of scattered radiation as compared to the total radiation impinging onto the X-ray detector.

11. The method according to claim 5, wherein
    detecting the direct X-radiation and the scattered X-radiation via the X-ray detector includes using an anti scatter grid to provide an attenuation of scattered X-rays impinging onto the X-ray detector.

12. The method according to claim 5, wherein
    obtaining a second gain dataset comprises acquiring the second gain dataset by an experimental recording of the predetermined object and preventing direct X-radiation from being impinged onto the X-ray detector via the presence of the predetermined object within radiation paths between the x-ray source and the x-ray detector.

13. The method according to claim 12, wherein
    combining the first gain dataset with the second gain dataset comprises adding the first gain dataset and the second gain dataset.

14. A method for obtaining a gain corrected X-ray image of an object under examination, the method comprising the steps of
    determining a gain dataset representing the gain coefficients of a two-dimensional X-ray detector by carrying out a method for determining a gain dataset representing gain coefficients of a two-dimensional X-ray detector being used for X-ray imaging, the method comprising: (i) providing a first gain dataset representing a first X-ray image (G(x,y)), which is generated by direct X-radiation being emitted from an X-ray source and detected by the X-ray detector in the absence of an object of interest, (ii) obtaining a second gain dataset representing a second X-ray image, which is based on scattered X-radiation being emitted from the X-ray source and detected by the X-ray detector in the presence of a predetermined object, and (iii) combining the first gain dataset with the second gain dataset to obtain the gain dataset;
    acquiring a third dataset representing an X-ray image of the object under examination, which has been inserted in between the X-ray source and the X-ray detector; and
    obtaining a gain corrected dataset representing a gain corrected image of the object under examination by dividing the third dataset by the gain dataset.

15. The method according to claim 14, wherein
    the obtained X-ray image is used for a three-dimensional reconstruction of the object under examination.

16. The method according to claim 14, wherein
    detecting the direct X-radiation and the scattered X-radiation via the X-ray detector includes using an anti scatter grid to provide an attenuation of scattered X-rays impinging onto the X-ray detector.

17. The method according to claim 14, wherein
combining the first gain dataset with the second gain dataset comprises adding the first gain dataset and the second gain dataset.

18. A data processing device for determining a gain dataset representing gain coefficients of a two-dimensional X-ray detector being used for X-ray imaging, the data processing device comprising:
   a data processor adapted for performing the method as set forth in claim 1, and
   a memory for storing (i) the first gain dataset representing the first X-ray image, and (ii) the second gain dataset representing the second X-ray image.

19. Medical X-ray imaging apparatus, comprising
a data processing device according to claim 18, wherein the medical X-ray imaging apparatus comprises one selected from the group consisting of a computed tomography scanner and a C-arm system.

20. A non-transitory computer-readable medium embodied with a computer program that is executable by a data processor for determining a gain dataset representing gain coefficients of a two-dimensional X-ray detector being used for X-ray imaging, the computer program for performing the method as set forth in claim 1.

* * * * *